(12) United States Patent
Wang (10) Patent No.: US 8,709,789 B2
(45) Date of Patent: Apr. 29, 2014

(54) METHODS AND DEVICES FOR RAPID AND SPECIFIC DETECTION OF MULTIPLE PROTEINS

(75) Inventor: Yingjian Wang, Worcester, MA (US)

(73) Assignee: Hypromatrix, Inc., Holden, MA (US)

( * ) Notice: Subject to any disclaimer, the term of this patent is extended or adjusted under 35 U.S.C. 154(b) by 1372 days.

(21) Appl. No.: 11/601,646

(22) Filed: Nov. 20, 2006

(65) Prior Publication Data

US 2008/0118983 A1     May 22, 2008

(51) Int. Cl.
*C12Q 1/00*      (2006.01)
*C12M 1/40*      (2006.01)

(52) U.S. Cl.
USPC ....... 435/287.1; 425/288.1; 435/7.1; 204/450

(58) Field of Classification Search
None
See application file for complete search history.

(56) References Cited

U.S. PATENT DOCUMENTS

| 4,493,815 | A * | 1/1985 | Fernwood et al. | 422/101 |
| 5,039,493 | A * | 8/1991 | Oprandy | 422/101 |
| 6,455,007 | B1 * | 9/2002 | Mansky et al. | 422/101 |
| 6,902,702 | B1 * | 6/2005 | Winegarden et al. | 422/100 |
| 2002/0008148 | A1 * | 1/2002 | Empedocles et al. | 235/494 |
| 2003/0082605 | A1 * | 5/2003 | Hodge | 435/6 |
| 2005/0030535 | A1 * | 2/2005 | Rassman et al. | 356/369 |
| 2005/0106621 | A1 * | 5/2005 | Winegarden et al. | 435/6 |

* cited by examiner

*Primary Examiner* — Jacob Cheu
*Assistant Examiner* — Carmencita M Belei
(74) *Attorney, Agent, or Firm* — Mirick, O'Connell, LLP (57) ABSTRACT

A method is provided for detecting multiple analytes via their interactions with reagents. The analytes are immobilized on an analyte support and are divided into subdivisions by a blotting apparatus. Reagents are applied, each to a specific subdivision of the analyte support and binds to the analytes there.

31 Claims, 6 Drawing Sheets

METHODS AND DEVICES FOR RAPID AND SPECIFIC DETECTION OF MULTIPLE PROTEINS

BACKGROUND

Proteins are important components of cells and their activities determine various cellular functions. Abnormal protein expression and activity may cause cell to malfunction. Although an organism' genome may encode tens of thousands of proteins, a given cell of the organism usually expresses only a fraction of the proteins; and the protein expression pattern determines a cell's shape and function. In biomedical research, it is usually desirable to know what proteins are expressed in a cell under a specific condition. By comparing protein expression profiles, it is possible to identify those proteins whose expressions and activations are responsible for the differences between cell types.

Diseases alter protein expressions and abnormal protein expressions are the causes of many diseases. Therefore, determination and comparison of the expression profiles between normal and abnormal biological samples are useful for understanding disease mechanisms. Simultaneous detection of multiple proteins is also useful in clinical diagnostics. For example, examining several viral proteins is more reliable than examining just one viral protein for the diagnosis of viral infection. Profiling protein expressions is also valuable in distinguishing normal cells from early-stage cancer cells, and from metastatic cancer cells. In addition, protein expression profiling is useful in key areas of drug development, such as in target selection, toxicology, and the identification of surrogate markers for drug response.

A protein with a specific amino acid sequence may be present in different isoforms due to posttranslational modifications. There are many types of protein posttranslational modifications including phosphorylation, glycosylation, lipidation, and ubiquitination. They play important roles in regulating protein activities and functions. Phosphorylation at serine, threonine or tyrosine residues is an important mechanism in signal transduction. Aberrant protein phosphorylation contributes to many human diseases. In a cellular process, certain proteins are characteristically modified and activated. Detection of these modified proteins can provide valuable information on that cellular process. Among the methods of detecting protein phosphorylations, metabolic labeling with radioisotopes and immuno-detection with antibodies against phosphoproteins are most commonly used. However, these methods are only applicable to the analysis of one or a few proteins at a time. Although antibodies specific for phosphorylated amino acids (e.g., PY20, 4G10) can reveal multiple phosphorylated proteins, they alone are unable to identify individual phosphorylated proteins. New methods for simultaneous detection of multiple phosphorylated or other modified proteins are highly desirable for signal transduction studies and clinical diagnosis.

It has long been the goal of molecular biologists to develop technologies that can reliably quantify the expressions of every protein and its isoforms in a biological sample. However, this has turned out to be difficult to achieve. Traditionally, the expression of one or a small number of proteins can be detected by immunological methods, such as Western blotting and Enzyme-Linked Immunosorbent Assay (ELISA). Western blotting (Immunoblotting) is a widely used technique in protein research. It combines the resolution of gel electrophoresis with the specificity of immunochemical detection and is powerful in determining a number of important characteristics of protein antigens, e.g., the relative molecular weight and the quantity of an antigen in a protein sample. When combined with immunoprecipitation, Western blotting allows very sensitive detection of low-abundant antigens and more importantly, the specific interactions between proteins. It is also useful in detecting protein posttranslational modifications, e.g., protein tyrosine phosphorylation (Kamps, 1991).

A standard procedure for Western blotting includes the steps of separating proteins by gel electrophoresis, transferring proteins from a gel to a membrane support, and detecting an antigen with its specific antibodies. Electrophoretic separation of proteins is usually performed in polyacrylamide gels. These gels are usually cast between a pair of glass plates by polymerizing a solution of acrylamide monomers into polyacrylamide chains and simultaneously cross-linking the chains into a semisolid matrix. The pore size of a gel can be varied by adjusting the concentrations of polyacrylamide and the cross-linking reagent. When a mixture of proteins is applied to a gel and an electric current is applied, smaller proteins migrate faster than larger proteins through the gel. Therefore, proteins are separated (distributed) in the gels according to their molecular weights.

Several strategies have been used to increase the throughput of Western blotting. In one method, a protein blot is probed with a mixture of two or more antibodies which bind to proteins at different molecular weight positions on the blot. The antibodies preferably contain no cross-reactivity so that the signal generated by each antibody can be easily identified. In another method, a blot can be sequentially probed with multiple antibodies. That is, after a blot is probed with an antibody, the antibody is stripped off the blot. Then, a different antibody is applied to the blot. In a third method, the previously probed antibody can be left on the blot but its ability to generate signals is blocked before a new antibody is applied (Krajewski, Zapata, and Reed, 1996. Analytical Biochemistry 236, 221-228).

Another strategy to increase the efficiency of Western blotting is to use a device to facilitate the probing of multiple proteins on the same protein blot. Such a device contains multiple compartments. When assembled with a protein blot, the device divides the blot into many separate locations, each being enclosed by a compartment. Antibodies are applied to the compartments, each to a different one so that it reacts with its specific antigen at a blot location enclosed by the compartment. One such device is Multiscreen Blotting apparatus from Bio-Rad (Hercules, Calif.). The apparatus comprises two major parts: a base plate and a sample plate. The sample plate contains many channels/compartments arranged in parallel columns. Each column has one channel, which is open at one side and closed at the other side. The closed side has two outlets through which solutions can be introduced to and removed from the channel. When a protein blot is placed between the base plate and the sample plate, the channels divide the blot into multiple leak-proof, enclosed areas. Antibody solution introduced into a channel will only react with the antigens enclosed by that channel. When a plurality of antibodies are applied to the channels, each to a different channel, multiple antigens can be detected on the sample blot, each at a specific location enclosed by a channel.

The channels in the Multiscreen Blotting apparatus are arranged vertically with each channel spanning a full vertical position. When assembled with a protein blot formed by transferring proteins from one-dimensional SDS-polyacrymide gel, each channel covers proteins with a full-range of molecular weights. Multiple Blotting apparatus is not suitable for the protein blots formed by transferring proteins from two-dimensional gels. The number of channels in the current device is small, up to a few dozens. Multiscreen blotting apparatus from Bio-Rad has 20 channels. The current device is usually used with a protein blot transferred from a curtain SDS-polyacrylamide gel. Therefore, only one protein sample can be analyzed in each blot. Another disadvantage of the current method is that antibodies have to be introduced to each channel individually. This becomes cumbersome when a large number of antibodies are used.

Many proteome analyses are carried out with two-dimensional (2D) gel electrophoresis for protein separation followed by mass spectrometry for protein identification. 2D gel electrophoresis requires more complicated procedures than one-dimensional gel electrophoresis and it is necessary to determine the identities of the proteins displayed on the two-dimensional gel, which is difficult to achieve for many proteins especially lower-abundance, basic and membrane proteins. Furthermore, despite the high resolving capability of 2D gel, multiple proteins are frequently found in one 2D gel spot so that quantitative and comparative analysis of 2D gel is prone to mistake. Protein identification by mass spectrometry-based technologies has improved significantly in recent years with the introduction of matrix-assisted laser-desorption ionisation/time-of-flight and electrospray ionisation methods.

Partly encouraged by the success of DNA microarrays in profiling mRNA expressions, strategies have been developed to use protein arrays in parallel examination of proteins. Protein arrays have been used for examining protein expression, protein phosphorylation, protein-protein interaction, protein-DNA interaction, and protein-analyte interaction (Lueking, et al. 1999. Protein microarrays for gene expression and antibody screening. Anal. Biochem. 270, 103-111. Ge, 2000 UPA, a universal protein array system for quantitative detection of protein-protein, protein-DNA, protein-RNA and protein-analyte interactions. Nucleic. Acid Research. 28, e3. Zhu, H. et al., 2001 Global analysis of protein activities using proteome chips. Science 293, 2101-2105. Wang et al. 2000 Stat1 as a component of tumor necrosis factor alpha receptor 1-TRADD signaling complex to inhibit NF-kappaB activation. Mol. Cell. Biol. 20, 4505). However, there are several difficulties that prevent protein arrays from becoming a quantitative tool. Notably, due to the non-specific binding of capture reagents (e.g. antibodies), protein arrays lack specificity in examining protein expressions. Additional protein identification criteria are needed to increase assay specificity.

Other methods have also been used for examining protein expressions and functions. Immunochemical staining is a versatile technique in determining both the presence and localization of an antigen (Harlow and Lane, Antibodies, a laboratory manual, Cold Spring Harbor Press, 1988). An antibody array-based staining method was also developed for examining protein expression, protein cellular and subcellular localization, and other protein properties (Wang, 2004, Immunostaining with dissociable antibody microarrays. Proteomics 4, 20-26).

PURPOSE OF THE INVENTION

It is an object of the present invention to describe a method for simultaneous detection of a plurality of analytes. In particular the invention teaches the use of a blotting apparatus to detect multiple proteins which are immobilized on a membrane support after they are separated by gel electrophoresis according to molecular weight and/or isoelectric point.

It is also an object of the invention to teach the use of reagent arrays to detect a plurality of analytes. Further objects and features of the invention will become apparent from a consideration of the ensuring description.

SUMMARY

The invention provides a method to facilitate the detection of a large number of proteins and other biological molecules. In the method, proteins in a biological sample are immobilized onto a solid support to form a protein blot. The protein blot is assembled with a blotting apparatus that contains multiple compartments arranged in rows and columns. The blotting apparatus thus divides the blot into many subdivisions. Antibodies are added to the apparatus, each in a different compartment to allow the antibody to bind its respective antigens in that compartment. The proteins can be first separated and then transferred and immobilized on a support. The separation can be by gel electrophoresis according to proteins' molecular weight or isoelectric point. Sodium dodecyl sulphate-polyacrylamide gel electrophoresis (SDS-PAGE) and two-dimensional gel electrophoresis are often used. In the method, two or more samples can be separated on the same SDS-PAGE gel; each is loaded in a different lane. In the method, before separation by gel electrophoresis, a subpopulation of the protein samples can be obtained by immunoprecipitation with antibodies. The antibodies can be against phosphorylated amino acids, including tyrosine, serine and threonine. The antibodies can also be against other protein posttranslational modifications, including ubiquitination.

In the method the blotting apparatus may comprise a base support and a separator, which contains rows and columns of compartments. When the analytes on an analyte support is assembled between the base support and the separator, the blotting apparatus divides the analyte support into multiple areas, each compartment enclosing one area. The compartments are usually elongated-shaped including a rectangular shape. The compartments are open either at one side or at both sides. The number of the compartments is from 4 to 100,000. The size of the compartments is from several microns to several centimeters in width and length. Preferably, the size of the compartments is from 1 millimeter to 10 millimeter in width, length, and depth. The apparatus can have 3 rows and 3 or more columns of compartments. The apparatus can have 4 rows and 5 or more columns of compartments. The apparatus can have 5 rows and 10 or more columns of compartments. The apparatus can have 6 to 10 rows and 10 or more columns of compartments. The apparatus can have 6 to 100 rows and 10 or more columns of compartments. The compartments can be arranged in a zigzag pattern. The zigzag step can be from 0.1 mm to 1 cm. The compartments can be arranged in a staggered pattern and the stagger step can be from 0.1 mm to 1 cm. The blotting apparatus can further comprise a top plate. The top plate contains a plurality of outlets. After assembly with the Separator, each compartment has two outlets. The width, length and height of the compartment range from 10 micrometer to 10 centimeter.

Reagent arrays can be used in the method. In one embodiment, the reagents are arranged on a reagent support according to the positions of their binding analytes on an analyte support. When the reagent array and the analyte on an analyte support are assembled with a blotting apparatus, each reagent will be in the same compartment as its binding analytes. The binding analytes can be separated according to molecular weight and immobilized on a analyte support. Or the binding analytes are separated according to isoelectric points and immobilized on an analyte support. Or the binding analytes are separated according to molecular weight and isoelectric points and immobilized on an analyte support.

To examine the presence of a plurality of analytes, the method include the steps of providing an array of reagents immobilized on a reagent support; providing analytes immobilized on an analyte support; providing a blotting apparatus which comprises a Separator that has rows and columns of compartments; assembling the array of reagents, the analytes on the analyte support and the blotting apparatus so that a member of the reagents and its binding analytes are in the same compartment; providing conditions so that reagents dissociate from the reagent support and bind to the analytes. The analyte support and the reagent support can be placed on the same side of the Separator. Or the analyte support and the reagent support are placed at the opposite side of the Separator.

DESCRIPTION OF THE PREFERRED EMBODIMENTS

The invention relates to novel methods of detecting biological molecules, in which multiple analytes are detected via their interactions with reagents. The term "analyte" as used herein refers to any biological molecules. One example is the proteins present in a protein lysate. The term "reagents" as used herein refers to any molecules of biological interest that is interactive with one or more analytes. Reagents include but are not limited to antibodies, recombinant proteins, synthetic peptides, DNA, RNA, nucleotides, and small chemicals. Antibodies can be directed against cellular proteins. In one embodiment, antibodies are against posttranslational modified proteins, e.g., phosphorylated proteins.

The Analytes

In a preferred embodiment, analytes are proteins, which can be a lysate from a cell line or a tissue. Protein lysates are prepared from cells or tissues by lysis with a buffer containing detergents such as sodium dodecyl sulphate (SDS), Triton X-100, and Nonidet P-40 (NP40). In many applications only a subgroup of a protein sample is desired for analysis. Such subgroup includes but is not limited to tyrosine phosphorylated proteins, phosphorylated proteins, unbiquitinated proteins, proteins interacting with a protein of interest, proteins interacting with a small molecular. Many methods are available for isolating a subgroup of proteins. These methods include but are not limited to affinity-purification. For example, anti-phosphotyrosine antibodies can be used to immunoprecipitate tyrosine phophosphorylated proteins from the total proteins. The proteins that interact with a protein of interest can be affinity-purified with an antibody specific for the protein of interest.

Proteins may be first separated and then immobilized on a support. Many methods for protein separations are known in the art. One-dimensional sodium dodecyl sulphate-polyacrylamide gel electrophoresis (SDS-PAGE) according to molecular weight is one of the mostly used methods. Proteins may also be separated by two-dimensional gel electrophoresis according to their molecular weight and isoelectric point. Other methods, such as liquid chromatograph are also commonly used. In one preferred embodiment, a protein sample is loaded onto a SDS-polyacrylamide gel that contains a wide well (the commonly referred curtain gel). In another preferred embodiment, two or more protein samples are loaded onto the adjacent wells of a gel. After transfer, the proteins in these samples can be analyzed side by side on the same protein blot.

In the methods, analytes are immobilized on an analyte support. The term "immobilization" is used herein, means the restriction of a reagent or an analyte on a solid support so that the movement of the reagent or analyte on the support is limited. For example, when an antibody is immobilized on a support, the antibody is attached to the support so that it may not dissociate from the support and the movement of the antibody on the support is also limited.

Protein lysates may be evenly placed on a support and immobilized on it. In many applications, proteins are first separated, e.g., by SDS/PAGE. After separation, proteins are transferred from gel to a solid support, such as a nitrocellulose membrane or a polyvinylidene difluoride (PVDF) membrane, which binds the proteins as they migrate out of the gel. Methods are known in the art to transfer proteins from a gel to a solid support. Transfer can be either performed by "wet" or "semidry" apparatus. A standard transfer buffer for wet transfer contains Tris, Glycine, and Methanol. The gel is placed in a transfer apparatus sandwiched between layers of filter paper and sponge with a membrane placed directly against the gel on the side facing the positive electrode. After a couple of hours, most proteins should be off the gel and bound to the membrane.

The analyte support can be made from a variety of materials including but are not limited to nitrocellulose, PVDF, Nylon, glass, bicarbonate, and gold. Protein immobilization on the support can be via non-covalent bond. The immobilization can be strengthened via covalent bond. Methods of protein immobilization by non-covalent and covalent bonds are known in the arts.

The Reagents

In a preferred embodiment of the method, the reagents are in an array format so that a reagent does not commingle with other reagents during the storage and during detection procedure. The term "reagent array" as used herein refers to a device that comprises a solid reagent support and a plurality of reagents on said solid reagent support; each of the reagents is at a pre-determined position. For example, antibodies may be deposited and immobilized on a reagent support to make an antibody array, each antibody at a predefined position so that it can be identified by a specific position on the antibody array.

The term "reagent support" is used herein, for the purposes of the specification and claims, to mean the structure on which reagents are deposited and immobilized. In the preferred embodiments, the reagent supports may be, but are not limited to, rigid plates made of glass or plastics and membranes made of plastics, papers, nitrocellulose, nylon, polyvinylidene difluoride (PVDF), or their derivatives. Membranes are easy to handle and reagents can be readily immobilized on them. Glass or plastic plates provide rigid support and are necessary in some applications.

A reagent support may be treated so that reagents can be immobilized with adequate strength suitable for specific applications. One way to treat a solid reagent support is to coat it with a layer of polymers that in turn will interact with reagents through non-specific, non-covalent bonds. For example, polymers comprising polylysine or polyethyleneimine may be used to coat glass slides or coverslips for use in immobilizing biological molecules.

Methods are available for depositing and immobilizing reagents on reagent supports to make reagent arrays. Reagents can be immobilized on a support via non-covalent or covalent bonds. Several techniques are available for depositing and immobilizing a plurality of biological reagents on solid supports, such as those described by Lehrach, et al. (Hybridization fingerprinting in genome mapping and sequencing, genome analysis, Vol. 1, Davies and Tilgham, Eds, Cold Spring Harbor Press, pp. 39-81, 1990) and Brown et al. (U.S. Pat. No. 5,807,522). Each of the aforementioned articles is incorporated by reference in its entirety. Reagents can be deposited manually onto a support and simply dried for immobilization. Nanoliter volumes of antibodies in an aqueous solution can be printed on a glass slide using a robotic arrayer. Therefore, arrays of biological reagents may be formed by depositing a plurality of reagents onto a flat solid support, one or a few reagents at a time, and each reagent at a pre-defined position.

The immobilization of reagents may be via adsorption (Trevan, 1980, Immobilized Enzymes: an introduction and their application in biotechnology. Wiley, Chichester). The adsorption forces involved may be nonspecific, hydrophobic or ionic interactions. Typically adsorbent materials used include, but are not limited to, clay, charcoal, hydroxyapatite, and most frequently, ion-exchange materials such as DEAE-Sephadex. Entrapment is another way to immobilize reagents (Trevan, 1980, Immobilized Enzymes: an introduction and their application in biotechnology. Wiley, Chichester). The entrapped reagents are not attached to the polymer; their free diffusion is merely restrained. One commonly used matrix is a polyacrylamide gel.

Reagents are immobilized on a solid support directly or indirectly. For example, reagents may be directly deposited at high density on a support, which can be as small as a microscopic slide. Technology has been developed for making high density DNA microarray (Shalon et al., Genome Research, 1996; 6: 639-645). Reagents may also be immobilized indirectly on the support. For instance, protein A or protein G, or their mutants can be first printed on a support as intermediates. Antibodies are then immobilized on the support through their interactions with protein A or G. One advantage of this method is that, by engaging the constant regions of antibodies with protein A or G, the variable regions of the antibodies (antigen-binding domains) will be fully exposed and available to bind antigens. Another advantage is that, since protein A or G can be modified to change their binding affinity for antibodies, when carefully designed mutants of protein A or protein G are used, antibodies can be immobilized on the support with desired strength. As such, antibodies on one hand can be immobilized on the support without losing positional information but on the other hand can leave the support and bind to other analytes of higher affinity. Recombinant fusion proteins are usually made to contain a tag (e.g. GST and 6Xhis) which specifically interacts with a ligand. They can be immobilized through the interactions between their tags and the ligands attached on the support. For example, Ligands (e.g., glutathione or nickel) can be first attached on a support and then recombinant fusion proteins containing a tag (e.g., GST or 6xHis) are immobilized on the same support via interacting with the ligands. The tags and the ligands can be modified to change their affinities so that the immobilization will have desired strength.

The amount of reagent immobilized at each spot can be varied. It can be from a few pico-grams to a few milligrams, depends on applications and the properties of the reagents and supports.

Reagents are usually deposited on a support as circular dots. The diameters of the dots range from a few microns to a few centimeters. Reagents can also be deposited in other shapes. For example, reagents can be immobilized in an elongated shape, such as a rectangular shape of a few microns to a few centimeters wide and a few microns to a few centimeters long. Different reagents can be deposited on a support in different shapes: some in circular dots, some in rectangular shapes; and the size of differently shaped dots may also be different. When proteins are separated by 2D-gel, because of the difference in abundance and properties, they are present in the gel (and protein blot after transfer onto a membrane support) as different-sized and different-sized spots. Therefore, arrays with different-sized and different-shaped antibody spots may be used with protein blots transferred from 2D gel.

In the method of the present invention, reagents are generally immobilized at positions that when the reagent support is aligned with the analyte support, each of the reagents is at a proper position to interact with its analyte. Therefore, a specific reagent may be immobilized at a specific position that is determined by the position of its binding analyte. For example, when proteins are separated by SDS/PAGE, transferred and immobilized on a support; each protein is immobilized at a specific position determined by its molecular weight: larger proteins are at upper parts of the support while smaller proteins are at the lower parts of the support. An antibody array used with such protein blot should have antibodies against larger antigens immobilized on the upper part of a support while antibodies against smaller antigens immobilized on the lower part of the support. When antigens are first separated by two-dimensional gel electrophoresis, transferred and immobilized on a membrane support; each antigen is immobilized at a specific position determined by its molecular weight and isoelectric point. Correspondingly, on an antibody arrays to be used with such protein blot, each of the antibodies can be immobilized according to the position of its antigen on the antigen support.

When a reagent support and an analyte support are assembled and aligned, each reagent is in the vicinity of its binding analyte. In the method of the invention, it is not necessary that a reagent and its binding analyte are in very close position, as long as under experimental condition the reagent can bind to the analyte. When the reagent support and analyte support are assembled in a blotting apparatus, a reagent can interact with its binding analyte if they are in the same compartment.

In the method, reagent immobilization is temporary: under specific releasing conditions, the immobilized reagents can dissociate from the reagent support. The physical and chemical nature of the immobilization determines whether an immobilized reagent can dissociate from the support; and how efficient the dissociation will be. When reagents are immobilized on a support by weak non-specific binding, they can be dissociated from the support by solubilization in a buffer. A commonly used buffer is phosphate-buffered saline (PBS). If reagents are immobilized via specific chemical interaction with a support, a chemical compound can be used to break the interaction and thus release the reagents from the support into the solution. Chemical compounds that can be used for this purpose includes but are not limited to biotin, glutatheonine, nickel, reducing agents (e.g. beta-mecaptoethanol). Methods are available in the prior arts to used solutions containing these chemicals to break covalent and non-covalent bonds.

The Blotting Apparatus

Figure 1:
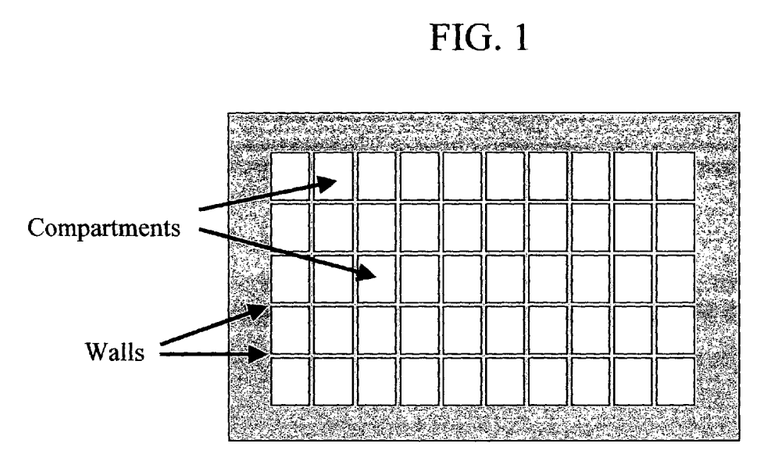
FIG. 1 shows a schematic view of a Separator which has compartments arranged in a regular pattern.

In the method, a blotting apparatus is used. In a preferred embodiment, the blotting apparatus comprises a Separator and a Base Support. FIG. 1 shows the perspective view of a Separator. A Separator comprises a lattice of compartments, with each compartment being open at one side or being open at both sides. The compartments can be of any shapes, although an elongated shape is preferred. In one embodiment, the compartments have a rectangular shape. The dimension of the compartments can vary considerably, ranging from several microns to several centimeters in width, length and depth. A preferable dimension is from several millimeters to several centimeters in width, length and depth. In one embodiment, the compartments are 10 micron to 1 millimeter in width, length and depth. In another preferred embodiment, the compartments are 1 millimeter to 10 millimeter in width, length and depth. The thickness of the walls separating the compartments can vary from 1 micron to several centimeters, although the preferable thickness ranges from 0.1 millimeter to 5 millimeters.

Figure 2:
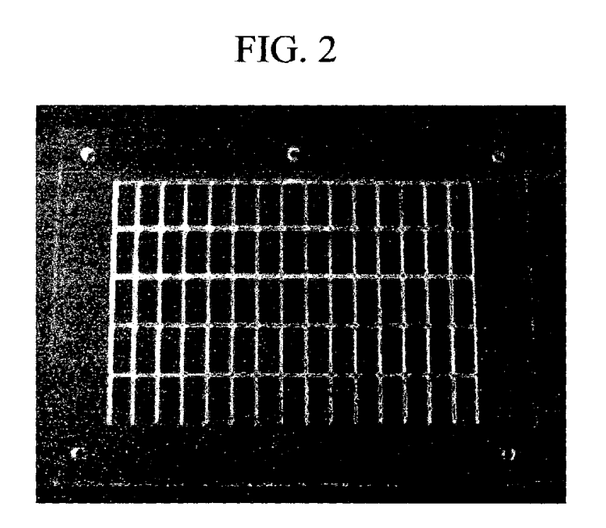
FIG. 2 shows a photo of a Separator which has compartments arranged in a regular pattern.

The compartments in the Separator can be arranged in a variety of configurations, but preferably in rows and columns. In a preferred embodiment, the compartments in a Separator are arranged in parallel columns and parallel rows. The compartment columns and rows are perpendicular to each other (FIG. 1 and FIG. 2). There are may be 1 to 1,000 compartments in each compartment column, and 2 to 100,000 compartments in each compartment row. In one embodiment there are 3 rows and 3 or more columns of said compartments. In another embodiment, there are 4 rows and 5 or more columns of said compartments. In another embodiment, there are 5 rows and 10 or more columns of said compartments. In another embodiment, there are 6 to 10 rows and 10 or more columns of said compartments. In another embodiment, there are 6 to 100 rows and 10 or more columns of said compartments.

Figure 3:
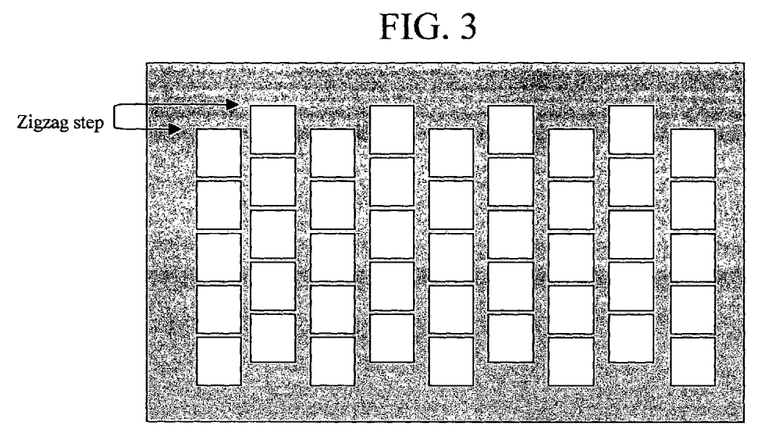
FIG. 3 shows a schematic view of a Separator which has compartment columns arranged in a vertical zigzag pattern.

When a protein blot is assembled with a Separator that has perfect perpendicular rows and columns of compartment, because of the walls between the compartments, proteins with certain molecular weights on the blot may be too close to the walls or even blocked by the walls. In one preferred embodiment, the compartments have the same size and they are arranged in a vertical zigzag pattern in which the neighboring columns shift up or down vertically in a fixed length (zigzag step) (see FIG. 3). The arrangement of the compartments in a zigzag pattern will ensure that every protein can be at the center portion of a compartment. The zigzag step can be from a few micrometers to a few centimeters. In an embodiment the zigzag step is from 0.1 mm to 1 cm. In a preferred embodiment, the zigzag step ranges from one-quart-length to one full-length of a compartment. In another preferred embodiment, the zigzag step ranges from one-half to a three-quart-length of a compartment. In another preferred embodiment, the zigzag step is approximately one half the length of a compartment.

Figure 4:
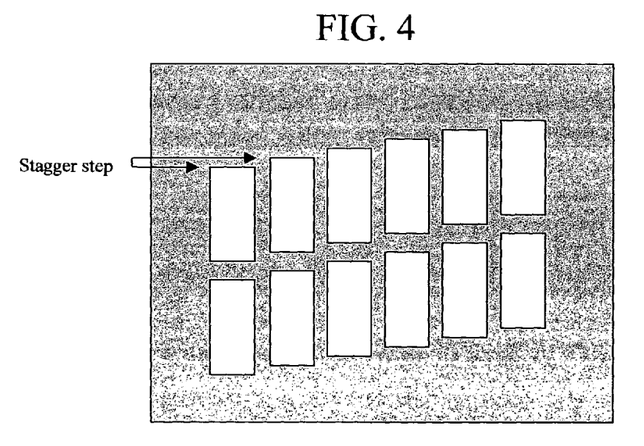
FIG. 4 shows a schematic view of a Separator which has compartment columns arranged in a staggered pattern.
Figure 5:
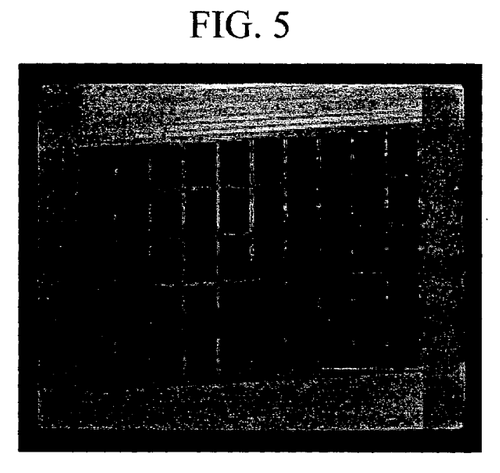
FIG. 5 shows a photo of a Separator which has compartment columns arranged in a staggered pattern.

In another preferred embodiment, the compartments have the same size and the compartment columns are arranged in a staggered pattern (see FIG. 4 and FIG. 5). Similar to the arrangement in a zigzag pattern, the arrangement of the compartments in a staggered pattern will ensure that every protein can be at the center portion of a compartment. The stagger step (the shift in vertical position between the neighboring compartment columns) can be from a few micrometers to a few centimeters. In an embodiment, the compartments are arranged in ascending or descending staggered manner with a stagger step of 0.1 mm to 1 cm. In a preferred embodiment, the total length of the stagger steps between the first and the last compartment ranges from one-quart-length to one full-length of a compartment. In another preferred embodiment, the total length of the stagger steps between the first and the last compartment ranges form one-half to a three-quart-length of a compartment. In another preferred embodiment, the total length of the stagger steps between the first and the last compartment is approximately one half the length of a compartment.

The physical parameters of the compartments in a Separator relates to how the analytes are separated and immobilized. When a protein sample is separated on a curtain SDS-polyacrylamide gel and transferred onto a membrane, a suitable Separator may contain narrow compartments so that each protein blot can be divided into many areas by the compartments and more protein can be analyzed on one blot. When two protein samples are loaded into the same SDS-polyacrylamide gel and transferred to a membrane support, a suitable Separator should contain compartments, each of which can cover an area with the width of two protein lanes so that a protein can be analyzed in the two samples side by side in the same compartment. Likewise, when three samples are to be analyzed, each compartment of a suitable Separator should cover the area of three protein lanes.

In another preferred embodiment, a Separator has differently shaped compartments and the dimensions of the compartments may also vary. The compartments may be arranged in an irregular pattern. Such a Separator is useful when used with a protein blot which is produced by transferring proteins from a gel after they are separated by two-dimensional gel electrophoresis according to both molecular weight and isoelectric point or by some other methods. The compartments are made in such a way that when assembled with a protein blot, each compartment will have the proper dimension, shape and position to enclose the intended antigen on the blot.

In a preferred embodiment, the compartments in the Separator are open at one side and closed at the other side. The open side makes contact with protein blot. Two outlets can be added in the closed side through which solutions can be applied. The size of each outlet can be from less than a millimeter to several centimeters in diameter.

Figure 6:
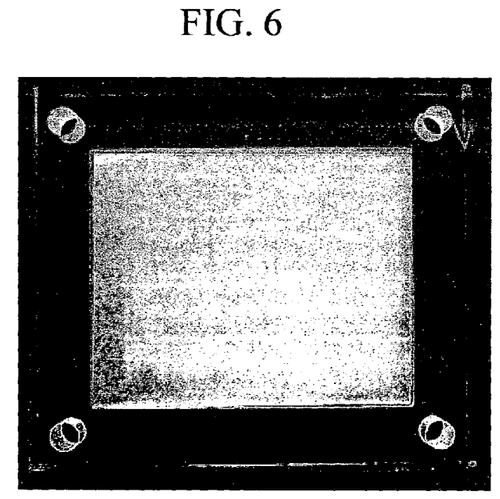
FIG. 6 shows a perspective view of a Base Support.

The Base Support holds the analyte support and with the Separator, forms leak-proof seal. FIG. 6 is a photo of a Base Support. The height of the Base Support may be from a few micrometers to several centimeters.

In another preferred embodiment, the blotting apparatus also include a Top Plate. A Top Plate is placed on top of the Separator. The Top Plate may contain outlets for each compartment so that solutions can be flowed in and out of each compartment. In an embodiment, each compartment has two outlets. The height of the Top Plate may be from 10 micrometers to several centimeters. Other features and mechanisms can be included in the Top Plate to facilitate the assembly of the apparatus or to facilitate the introduction of solutions into the compartments.

Many mechanisms are available to make a tight seal. For example, screws can be used at the four corners of the Separator and the Base Support to hold the components tight so that each compartment is leak-proof. Gaskets can be placed between the Base Support and the analyte support and/or between the analyte support and the Separator to prevent leakage. The gaskets can be made from silicone rubber or any other suitable materials.

The Base Support, Separator and the Top Plate can be made from materials selected from plastics, metal, alloys, etc.

The Procedure

A preferred method of the present invention comprises the steps of providing analytes immobilized on an analyte support; providing a Separator which has multiple rows of compartments; assembling said Separator with said analyte support, wherein each of said compartments encloses a portion of the immobilized analytes; applying reagents, each in a compartment so that a reagent and its interacting analytes are in the same compartment and do not commingle with the reagents enclosed in other compartments during the procedure.

In one preferred embodiment, the parallel compartments are arranged in a vertical zigzag pattern. The zigzag step can be from a few micrometers to a few centimeters. In an embodiment the compartments are arranged in a zigzag pattern with an step of 0.1 mm to 1 cm. In a preferred embodiment, the total length of the steps ranges from one-quart-length to one full-length of a compartment. In another preferred embodiment, the total length of the steps ranges from one-half to a three-quart-length of a compartment. In another preferred embodiment, the total length of the steps is approximately one half the length of a compartment.

In another preferred embodiment, the compartment columns are arranged in a staggered pattern. The stagger step can be from a few micrometers to a few centimeters. In an embodiment, the compartments are arranged in a staggered manner with a staggered step of 0.1 mm to 1 cm. In a preferred embodiment, the total length of the staggered steps between the first and the last compartment ranges from one-quart-length to one full-length of a compartment. In another preferred embodiment, the total length of the staggered steps between the first and the last compartment ranges form one-half to a three-quart-length of a compartment. In another preferred embodiment, the total length of the staggered steps between the first and the last compartment is approximately one half the length of a compartment.

Figure 7:
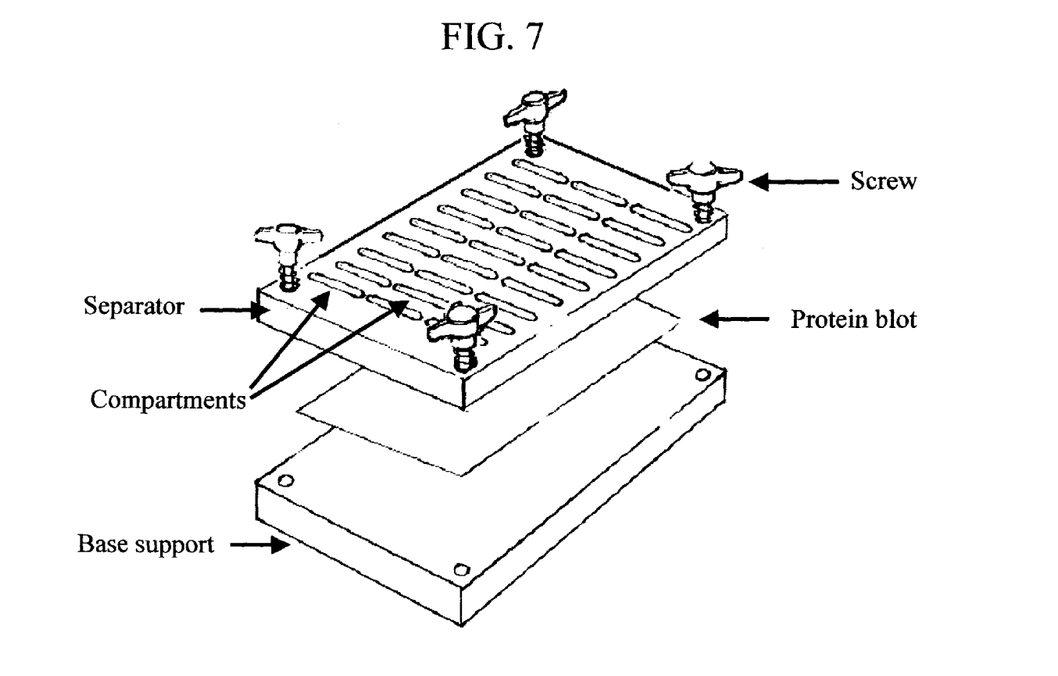
FIG. 7 shows a schematic view of the assembly of a Base Support, a membrane analyte support, and a Separator.
Figure 8:
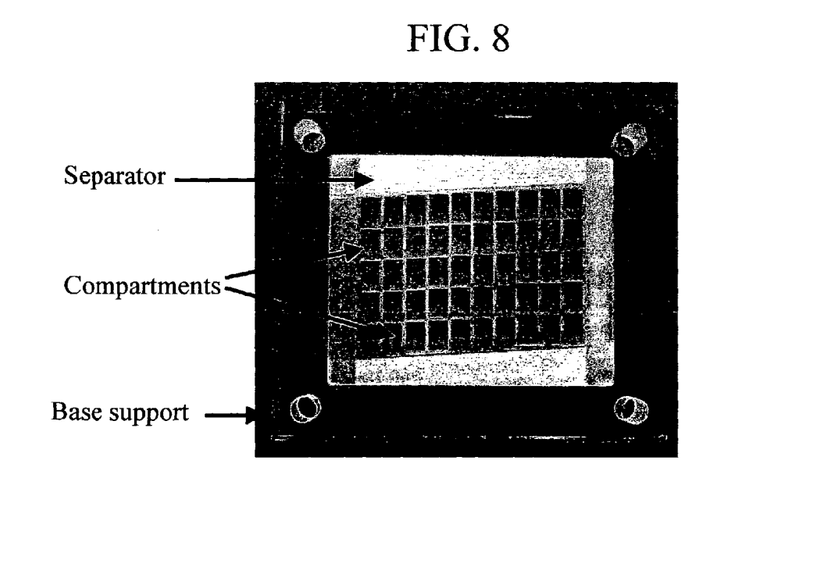
FIG. 8 shows a photo of the assembly of a Base Support, a protein blot membrane and a Separator.

FIG. 7 shows the assembly of various components in a preferred embodiment of the method. A membrane analyte support is placed on a Base Support; a Separator is placed on the analyte support. The Separator and the Base Support are held together tightly so that the membrane analyte support is divided into many areas, each being enclosed by a compartment. FIG. 8 shows a photo of the assembly of a Base Support, a protein blot and a Separator. The protein blot is sandwiched between the Base Support and the Separator and could not be seen in the photo.

Reagents can be applied to the compartments, each into a specific compartment. During incubation, the analytes enclosed by a compartment will react with the reagents applied into that compartment. Because of the tight seal by the Separator and the Base Support, there is no significant leakage of reagents between compartments. To facilitate reagents binding to their antigens, solutions can be agitated, e.g. by shaking.

Reagent solutions can be applied to the compartments manually or automatically using a robot. Many designs and systems are available for this purpose. A robotic system usually contains a liquid dispensing device and a programmable moving mechanism to move the liquid dispensing device to the proper positions to apply solutions to the compartments or take solutions out from the compartments. In another preferred embodiment, a special device is used to facilitate the application of solutions to the compartments.

After binding occurs between the reagents and the analytes, the reagent solution can be removed from compartments, e.g., via pump. Washing solution is introduced into and taken out from the compartments to remove any unbound reagents. Solutions can be added to each compartment by positive or negative pressure. To facilitate reactions solution can be agitated, moved back and forth, e.g. by pump.

The reagents bound to the analyte support can be detected. From the amount of the reagent bound to an analyte, the concentration of the analyte in the original analyte sample can be derived. Many known arts can be used to detect primary antibodies. A common method is to use enzyme-conjugated secondary antibodies, such as horseradish peroxidase or alkaline phosphatase conjugated goat anti-rabbit and goat anti-mouse antibodies. Substrates such as Supersignal chemiluminescence substrates from PIERCE can be used. Fluorescent-labeled secondary antibodies can also be used. The fluorescent signals can be detected with a camera or a fluorescence scanner. Other technologies that can be used include immuno-PCR (Sano et al., 1992, Science 258, 120-122), rolling circle DNA amplification (Schweitzer et al., 2000, Proc. Natl. Acad. Sci. USA 97, 10113-10119), and immuno-detection amplified by T7 RNA polymerase (Zhang et al., 2001, Proc. Natl. Acad. Sci. USA, Vol. 98, 5497-5502.). Enzyme- or fluorescence-conjugated secondary antibodies can be added to the compartments. After incubation, unbound secondary antibodies are washed off. Enzyme substrate can be then added and signals are detected. The protein blot can be removed from the assembly and placed in a different container before signals are detected.

Using Reagent Arrays

In a preferred method, reagent arrays are employed. The method comprises the steps of providing a reagent support on which one or more reagents are immobilized; providing an analyte support on which a plurality of analytes are immobilized; providing compartments so that each a reagent and its interacting analytes are in one compartment and do not commingle with other reagents enclosed in other compartments during the procedure; applying releasing conditions whereby the reagents dissociate from the reagent support and bind to the analytes on the analyte support.

A Separator provides the compartments. The Separator may comprise 1 to 100,000 compartments in each column and 1 to 1,000 compartments in each row. The compartments may be arranged in a regular or a zigzag or a staggered pattern. When a reagent support and an analyte support are assembled with a Separator, the analyte at a specific position of the analyte support is contained in an enclosed compartment as its interacting reagent but not other reagent-analyte interacting pairs.

In a preferred embodiment, both the reagent array and the analyte support are placed between the base support and the Separator. The reagent array and the analyte support are placed between the Base Support and the Separator in such a way that an analyte at a specific position of the analyte support is contained in an enclosed compartment as its interacting reagent but not other reagents. The Separator opens at both sides or the Separator opens at one side and there are two outlets for each compartment on the other side so that solutions can be flowed in and out of each compartment. Gaskets can be used to prevent any leak.

In another preferred embodiment, analyte support and reagent support are placed at opposite side of a Separator, e.g., analyte support are placed between the base support and the separator; the reagent support is placed on top of the separator. In this configuration the reagent support can have concave shapes so that it curves into the compartments. Thus, when the reagent support is placed on top of the Separator, reagent immobilized on the support will be inside the compartment.

Figure 9:
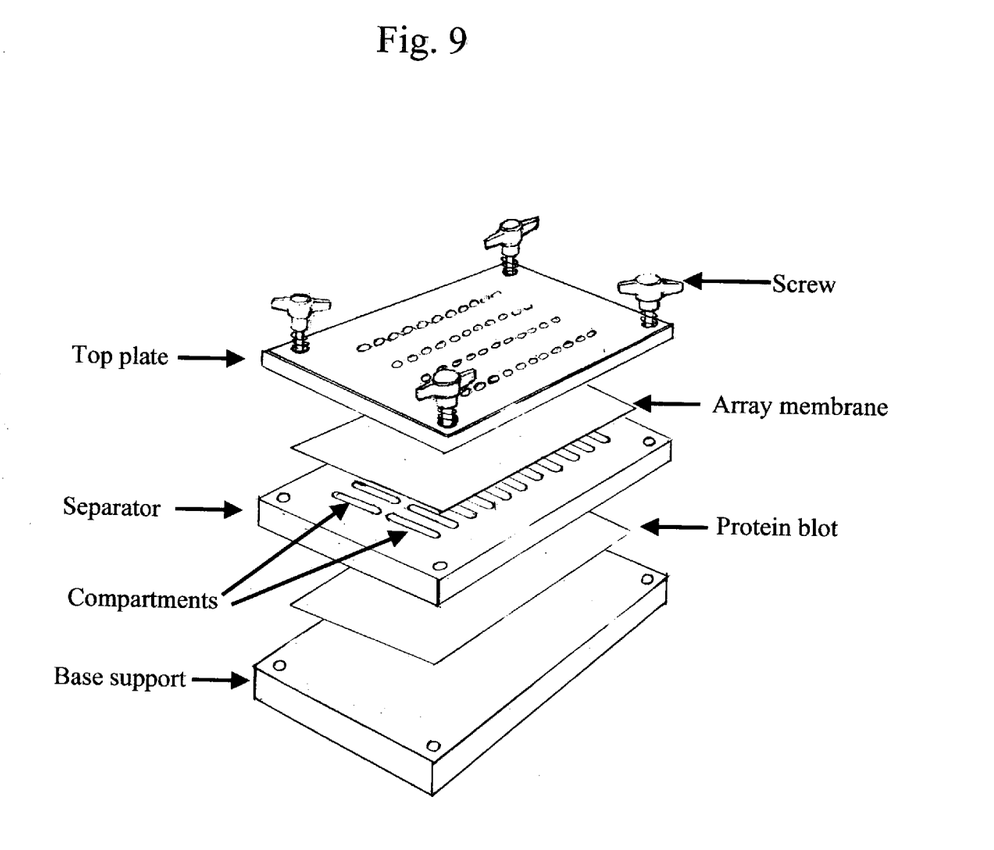
FIG. 9 shows a perspective view of the assembly of a Base Support, a membrane analyte support, a Separator, a reagent support, and a top plate.

In another embodiment a top plate can be added to facilitate assay. FIG. 9 shows a perspective view of the assembly of a Base Support, a membrane analyte support, a Separator, a reagent support, and a Top Plate. In the Top Plate, there are two outlets for each compartment so that solutions can be flowed in and out of each compartment.

There are many design and configurations for the blotting apparatus. Variations from the examples are obvious to the person skilled in the arts. For example, the top plate of the blotting apparatus is also the reagent support. Reagents can be directly deposited onto the top plate, each reagent at a position that is enclosed by a different compartment. In another embodiment, the Separator is also the reagent support. Reagents can be directly deposited onto the Separator, each reagent at a position that is enclosed by a different compartment. The reagents can be deposited at the inside walls of the compartments. In another embodiment, the base is the analyte support. For example, after separation by SDS/PAGE, protein samples can be electro-transferred onto a solid support which is also used as the base support of the blotting apparatus.

After assembly, a releasing condition is applied, wherein; reagents will be solubilized and dissociated from the reagent support. One releasing condition is applying a solution that will solubilize the reagents from the reagent support. The solubilized reagents remain in the same compartment. During incubation, the reagents will bind to their interactive analytes which are immobilized on the analyte support, and which are enclosed in the same compartment. Due to tight seal by the Separator, there is no significant leakage of reagents between compartments.

After binding, the reagents and reagent support can be removed, and washing solution is introduced into the compartments to remove unbound reagents. Or the reagent support can remain in the blotting apparatus. After wash, all reagents will be washed away.

Antibody Immobilization

In one preferred embodiment, protein lysates are separated by SDS/PAGE and transferred to a membrane support to form a protein blot. Proteins with higher molecular weight are immobilized at the upper position of the blot while proteins with lower molecular weight are immobilized at the lower position of the blot. For an antibody array to be used with such protein blot, antibodies against high molecular weight proteins are immobilized at the upper position of the array support while antibodies against low molecular weight proteins are immobilized at the lower position of the array support. Thus when the protein blot and the antibody array are assembled in the blotting apparatus, each antibody and its antigen are in the same compartments. Antibody against antigens with similar molecular weight can be immobilized at the same horizontal positions (enclosed by the same compartment rows). Therefore, one transfer membrane can be divided into several groups, each group have antigens with similar molecular weights. Preferably, a membrane is divided into 1 to 10 groups.

The antibodies are fixed to the antibody support with strength sufficient to immobilize said antibodies before making enclosures and before applying a releasing condition and yet said bound antibodies can dissociate from said antibody support after applying the releasing condition.

When the protein blot is placed on top of a base support, the side of the blot with no immobilized proteins faces the base support and the side with immobilized proteins faces outward. A separator is then placed on the protein blotting membrane. The separator produces compartments, each of which encircles a specific area of the sample membrane. Each compartment has a rectangular shape. An antibody array of is then place on the top of the Separator. A top plate is then put on top of the array. The top plate comprises outlets through which solution can flow in and out of each compartments. Pressure can be applied (e.g., by tightening the screws) to make tight seal so that each compartment is leak-proof.

In one embodiment, each antibody is immobilized on a separate membrane support and each compartment contains one or more such membranes. In another embodiment, the antibodies are immobilized on one membrane support, each antibody at a specific pre-determined position. One or more antibodies can be immobilized at the position that is encircled by a compartment.

In one preferred embodiment, a protein lysate is separated by a SDS-polyacrylamide curtain gel. Then the proteins are transferred from the gel to a membrane support to form a protein blot. The protein blot is assembled between a Base Support and a Separator so that the compartments divide the blots into different areas. The blot and the Separator are aligned: the compartments at the upper portions enclose proteins with higher molecular weights while compartments at the lower portions enclose proteins with lower molecular weights. Antibodies are added to the compartments, each antibody is added to the compartment which encloses its antigen on the protein blot. Antibodies against higher molecular weight antigens are added to the compartments at the upper portions of the Separator while antibodies against lower molecular weight antigens are added to the compartments at the lower portions of the Separator. To compare protein expressions between two protein samples, each sample can be first separated by a SDS-polyacrylamide curtain gel and transferred to a membrane support. Each protein blot is then assembled between a Base Support and a Separator. The presence of each antigen in the protein samples is detected and compared. Using the same procedure, protein expression patterns in three or more protein samples can be detected and compared.

In another preferred embodiment, a protein lysate is separated by a SDS-polyacrylamide curtain gel. Then the proteins are transferred from the gel to a membrane support to form a protein blot. Antibodies against multiple proteins were immobilized on a reagent support to form an antibody array; the position of each antibody is predefined according to the position of its antigen on the protein blot. That is, antibodies against high molecular weight antigens are deposited on the upper part of the reagent support while antibodies against low molecular weight antigens are deposited on the lower part of the reagent support. The protein blot and the antibody array are assembled in the blotting apparatus so that compartment cover one antibody and part of the protein blot containing its antigen. The reagent support and analyte support are not in direct contact. Then PBS is introduced into each compartment to cover both the antibodies and the protein blot. The antibodies are released into the PBS and bind to its antigens on the protein blot during incubation. Agitation (e.g. by shaking) can be used to facilitate antibody release from the antibody support and to facilitate antibody binding to its antigen on the protein blot. To compare protein expressions between two protein samples, each sample can be first separated by a SDS-polyacrylamide curtain gel and transferred to a membrane support. Each protein blot is assembled with an identical antibody array in a blotting apparatus. The presence of each antigen in the protein samples is detected and compared.

Using the same procedure, protein expression patterns in three or more protein samples can be detected and compared.

In one preferred embodiment to compare protein expressions between two or more samples, the protein samples are separated on the same SDS-polyacrylamide gel and transferred to one analyte support. The protein samples are loaded to the neighboring lanes of a gel. Each protein in the samples is detected in the same compartment side by side. For example, to compare protein expression between two protein samples, the first sample is loaded in lanes 1, 3, 5, 7, 9 while the second sample in lanes 2, 4, 6, 8, 10 of the same gel. After separation by SDS-PAGE the proteins are transferred to a PVDF membrane. Then the protein blot is assembled between a Base Support and a Separator whose compartments have the width of two protein lanes so that each compartment will cover two lanes: one lane from each protein sample. Similarly, three or more protein samples can be separated on the SDS-polyacrylamide gel and transferred onto a membrane support. A Separator whose compartments can cover three lanes (for three protein samples) or more lanes (for more protein samples) will be used.

In another preferred embodiment to compare protein expressions between two or more samples, the samples are separated on the same SDS/PAGE gel and transferred to one analyte support. The protein samples are loaded to the neighboring lanes of the SDS/PAGE gel. Each protein in the two samples is detected in the same compartment side by side. For example, to compare protein expression between two protein samples, the first sample is loaded in lanes 1, 3, 5, 7, 9 while the second sample in lanes 2, 4, 6, 8, 10 of the same gel. After separation by SDS/PAGE the proteins are transfer to a PVDF membrane. Then the protein blot is assemble in the blotting apparatus with an antibody array in such as way the each compartment will exactly cover two protein lanes: one lane from each protein sample. Similarly, three or more protein samples can be separated on the SDS/PAGE gel and transferred onto on membrane support. The width of each compartment of the blotting apparatus will cover exactly three or more lanes, one lane from each sample.

In one preferred embodiment, tyrosine phosphorylation of multiple proteins can be detected. A protein lysate is prepared by lysing cultured cells or tissues. Lysate is then incubated with anti-phosphotyrosine antibody followed by incubation with protein G Sepharose beads. Anti-phosphotyrosine antibody can be covalently conjugated on Sepharose beads or other solid supports. Precipitated proteins are separated by SDS-PAGE and transferred onto a membrane support. After blocking with 5% nonfat dry milk in PBS, the blot is assembled between a Base Support and a Separator. After adding antibody solution to the compartments and incubation, PBS is used to wash. After that, the membrane is incubated with anti-rabbit or anti-mouse immunoglobulins conjugated with horseradish peroxidase. To compare protein phosphorylation patterns between two samples, phosphorylated proteins are purified using anti-phospho amino acid antibodies and each of the purified phosphoprotein samples is separated by a SDS-polyacrylamide curtain gel and transferred to a membrane (analyte support). Each protein blot is assembled between a Base Support and a Separator. The presence of each antigen in the protein samples is detected and compared. Using the same procedure, protein phosphorylation patterns in three or more protein samples can be detected and compared. Alternatively, two or more samples of affinity-purified phosphoryated proteins can be separated on the same SDS-polyacrylamide gel and transferred to one membrane support. The membrane is then assembled between a Base Support and a Separator. Using the procedure described above, a phosphorylated protein from two or more samples can be detected in the same compartment. Similarly other types of protein posttranslational modifications can be examined. Antibodies against other modified moieties will be used instead of anti-phosphotyrosine antibodies to obtain proteins with specific modifications. For example anti-ubiquintin antibodies can be used to purify ubiquintinated proteins and then the proteins can be further identified with the present method.

In another preferred embodiment for detecting tyrosine phosphorylation of multiple proteins, anti-phosphotyrosine antibodies are used to isolate phosphorylated proteins. Isolated proteins are separated by SDS-PAGE and transferred onto Immobilon-P membrane (Millipore Corp., Bedford, Mass.). After blockage with 5% nonfat dry milk in PBS, the membranes were assembled in a blotting apparatus with an antibody array containing antibodies against multiple proteins. After adding solution to the compartments and incubation, PBS is used to wash. After that, the membranes were incubated with anti-rabbit or anti-mouse immunoglobulins conjugated with horseradish peroxidase. To compare protein phosphorylation patterns between two samples, phosphorylated proteins are purified using anti-phospho amino acid antibodies and each purified phospohoprotein samples are separated by a SDS/PAGE curtain gel and transferred to a PVDF membrane (analyte support). Each protein blot is assembled with an identical antibody array in a blotting apparatus. The presence of each antigen in the protein samples is detected and compared. Using the same procedure, protein phosphorylation pattern in three or more protein samples can be detected and compared. Alternately, two or more samples of affinity-purified phosphoryated proteins can be separated on the same SDS/PAGE gel and transferred to one membrane support. The membrane is then assembled with an antibody array in a blotting apparatus. Using the procedure described above, a phosphorylated protein from two or more samples can be detected in the same compartment. Similarly other types of protein posttranslational modifications can be examined. Antibodies against other modified moiety will be used instead of anti-phosphotyrosine antibodies. For example anti-ubiquination antibodies can be used to purify ubiqunated proteins and then the proteins can be further identified with the present method.

In one preferred embodiment of the present invention, proteins interacting with a protein of interest are first purified by immunoprecipitation with the antibodies against the protein of interest. The purified proteins are then separated by SDS/PAGE and transferred to an analyte membrane support. The membrane is then assembled between a Base Support and a Separator. A positive detection of a protein in the purified samples would suggest that the protein interacts with the protein of interest.

In another preferred embodiment of the present invention, proteins interacting with a protein of interest are first purified by immunoprecipitation with the antibodies against the protein of interest. The purified proteins are then separated on SDS/PAGE and transferred to an analyte membrane support. The membrane is then assembled with an antibody array in a blotting apparatus. A positive detection of a protein in the purified samples would suggest that the protein interacts with the protein of interest.

EXAMPLES

The following examples are for illustration only and in no way are intended to limit the present invention. Although the examples describe the use of antibodies as reagents according to the invention, similar usage of reagents other than antibodies are obvious to the people familiar with the arts. Such reagents include but are not limited to recombinant proteins, recombinant antibodies, single chain antibodies, nucleic acids, oligos, cDNA probes, carbohydrates, lipids, small chemicals. For example, DNA probes instead of antibodies may be used to detect the presence of multiple DNA or RNA in the sample. To do so, DNA or RNA probes are immobilized on a solid support. Preferably, the immobilization of the probes is strong enough to maintain probes' positions on the support; but is preferably weak enough to be efficiently dissociated from the support into a solution under certain conditions. When an array of DNA or RNA probes made according to the present invention is used, the presence and quantities of a large number of DNA or RNA sequences can be detected. The methods for preparing DNA and RNA probes are known in the art (Ian A. Darby (Editor), In Situ Hybridization Protocols (Methods in Molecular Biology, 123), by Humana Press; 2nd edition, 2000).

With technologies in microfabrication and microfluidic control (Fundamentals of Microfabrication: The Science of Miniaturization, Second Edition, Marc J Madou, CRC Press 2002; Microfluidic Technology and Applications, by Michael Koch, et al., 2000, Research Studies Press), the blotting apparatuses described in this invention can be made at a scale of a few micrometers to a few centimeters. Thus the method can be performed with much less analytes and reagents. However, such variations will not change the functionality of the blotting apparatuses or the principles of the methods.

Example 1

Figure 10:
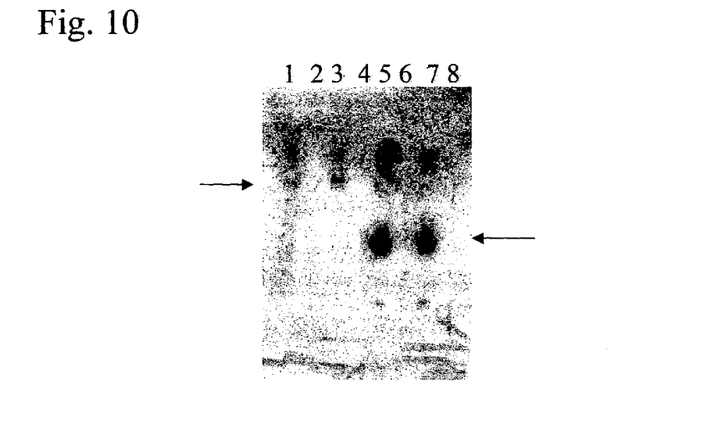
FIG. 10 shows an example of detecting protein expressions in a protein sample.

In this example (see FIG. 10), A431 cells were lysed in lysis buffer (1% SDS in PBS plus protease and phosphotase inhibitors) and the lysate were separated by SDS/PAGE using a curtain gel. Proteins were transferred and immobilized on a PVDF membrane. The blot was blocked in blocking solution (TBS-T, 5% non-fat dry powdered milk) for 1 hour at room temperature. Antibodies against 2 proteins were immobilized on a support in one row. The blot and antibody support were assembled in Multiple Screen apparatus from Bio-rad, with the antibody array aligned on the top of the protein blot so that it did not block the areas where antigens were to be detected. Both the proteins on the protein blot and antibodies on the antibody support face up so that they are accessible to the solutions. The distance between neighboring spots equals the width of two channels of the Multiple screen apparatus. Antibodies in solution were added to two channels. Channel 1, immobilized anti-cbl; channel 2, anti-cbl in solution; channel 3, immobilized anti-HSP70; channel 4, anti-HSP70 in solution. After binding of the primary antibodies, HRP-conjugated secondary antibodies were used and chemiluminescence system (ECL; Amersham Life Science, Buckinghamshire, UK) was used for protein detection. The expression of the ten proteins in A431 and ME180 cells were revealed side by side.

Example 2

Figure 11:
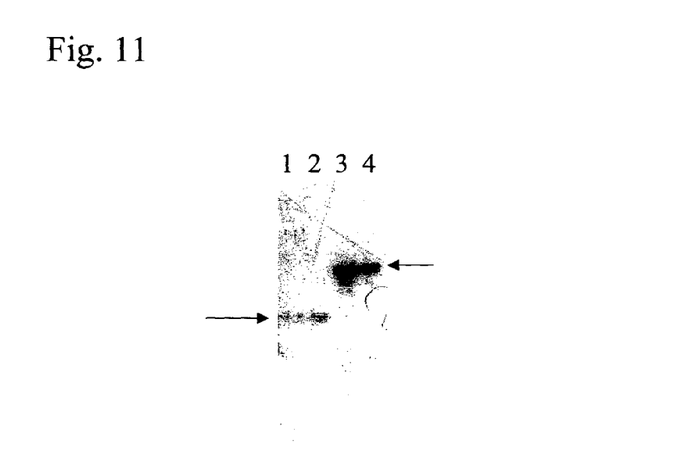
FIG. 11 shows another example of detecting protein expressions in a protein sample.

In this example (see FIG. 11), protein lysates of A431 cells were separated by SDS/PAGE using a curtain gel. Antibodies against 2 proteins were immobilized on a support at the same horizontal positions in one row. The protein blot and antibody array were assembled in a blotting apparatus with three layers: a base support, a separator and a top plate. The distance between the two antibody spots equals the width of two compartments in one row. Compartment 1 enclosed immobilized anti-Lyn while compartment 3 enclosed immobilized anti-Stat1. Solutions containing soluble anti-Lyn antibody and anti-Stat1 antibody were applied to compartment 2 and compartment 4, respectively. Both the immobilized antibodies and the antibodies in solution revealed their antigens.

Example 3

In this example, antibodies against 20 proteins were immobilized on a support in two horizontal rows, 10 vertical columns. Antibodies against larger proteins are at the upper row while antibodies against smaller proteins are at the lower row. Protein lysates of A431 cells were separated by SDS/PAGE using a curtain gel. The protein blot and antibody array were assembled in a blotting apparatus with three layers. The distance between the two antibody spots equals the width of each compartment. The immobilized antibodies revealed their antigens.

Example 4

In this example protein lysates of A431 and ME180 cells were separated by SDS/PAGE in the same gel side by side. A431 protein lysate is loaded in lanes 1, 3, 5, 7, 9 while ME180 protein lysate in lanes 2, 4, 6, 8, 10. After transfer to a PVDF membrane, the protein blot and antibody array were assembled in a blotting apparatus with three layers. Antibodies against 10 proteins were immobilized on a support in two rows, 5 columns. The distance between two antibody spots equals the width of each compartment and equals the width of two neighboring lanes of the SDS/PAGE so that each compartment enclosed one antibody spot and two neighboring lanes of the protein blot. After binding of the primary antibodies, HRP-conjugated secondary antibodies were used and chemiluminescence system (ECL; Amersham Life Science, Buckinghamshire, UK) was used for protein detection. The expression of the ten proteins in A431 and ME180 cells were revealed side by side.

Example 5

In this example, proteins interacting with Stat1 were examined. First protein samples were prepared by lysing A431 cells with a buffer containing 1% Triton in PBS plus protease inhibitors. Stat1 and its interacting proteins were precipitated by using Stat1 antibodies immobilized on agarose beads. The precipitate was then loaded on a SDS/PAGE curtain gel. After separation and transfer to a PVDF membrane, the blot was assembled in a blotting apparatus with an antibody array. The antibody array contains 50 antibodies in 10 rows and 5 columns. As can be seen in FIG. 8, several proteins were detected, suggesting that they interact with Stat1 in A431 protein lysate.

Example 6

In this example, tyrosine phosphorylated proteins were first purified by immunoprecipitation with anti-phosphotyrosine antibodies (PY20 immobilized on agarose beads) in the presence of protease and phophotase inhibitors (1.72 mM phenylmethylsulfonyl fluoride, 21 µM leupeptin, 10 µg/mL aprotinin, 10 mM sodium pyrophosphate, 10 mM sodium fluoride, and 1 mM sodium vanadate). Then they are separated by SDS/PAGE and transferred to a PVDF membrane. The blot was assembled in a blotting apparatus with an antibody array. The antibody array contains 50 antibodies in 10 rows and 5 columns. As can be seen in FIG. 9, several proteins were detected, suggesting that they are tyrosine phosphorylated.

Example 7

In this example, a blotting apparatus with two layers was used. Antibodies are directly deposited onto the inside wall of a separator and dried. Each antibody was deposited into a different compartment. Protein lysates of A431 cells were separated by SDS/PAGE using a curtain gel. The protein blot was assembled in a blotting apparatus between the base support and the separator. PBS was introduced into each compartment to solubilize the antibodies on the separator. After the antibodies were released into the PBS they bind to their respective antigens on the protein blot during incubation.

The invention claimed is:

1. A Western blotting apparatus for detecting a plurality of analytes, said blotting apparatus comprising a base support, an analyte support comprising a solid support on which said analytes are immobilized wherein the analyte support is formed by separating the analytes by gel electrophoresis according to their properties selected from the group consisting of molecular weights and isoelectric points and transferring the analytes from gel to said solid support; and a separator containing at least three rows and least two columns of rectangular-shaped compartments arranged in a pattern selected from the group consisting of zigzag pattern and staggered pattern, wherein, said analyte support is assembled between said base support and said separator, whereby each of said analytes is at the center portion of one of said compartments.

2. The separator of claim 1, wherein said blotting apparatus contains 3 to 10 rows and 10 or more columns of said compartments.

3. The blotting apparatus of claim 1, wherein said compartments are arranged in a zigzag pattern.

4. The blotting apparatus of claim 1, wherein said compartments are arranged in a staggered pattern.

5. The blotting apparatus of claim 3, wherein said zigzag pattern has a zigzag step of 0.1 millimeter to 1 centimeter.

6. The blotting apparatus of claim 3, wherein said zigzag pattern has a zigzag step of one-quart-length to a three-quart-length of said compartment.

7. The blotting apparatus of claim 3, wherein said zigzag pattern has a zigzag step of approximately one half the length of said compartment.

8. The blotting apparatus of claim 4, wherein said staggered pattern has a stagger step of 0.1 millimeter to 1 centimeter.

9. The blotting apparatus of claim 4, wherein the total length of the stagger steps between the first and the last compartment ranges from one-quart-length to one full-length of said compartment.

10. The blotting apparatus of claim 4, wherein the total length of the stagger steps between the first and the last compartment is approximately one half the length of said compartment.

11. The blotting apparatus of claim 1, further comprises a reagent support on which reagents are immobilized.

12. The Western blotting apparatus of claim 1, further comprising a reagent support on which reagents are immobilized and wherein said reagent support is placed on top of the analyte support on the same side of the separator.

13. The Western blotting apparatus of claim 1, further comprising a reagent support on which reagents are immobilized and wherein said reagent support is placed on top of the analyte support on the opposite side of the separator.

14. A Western blotting method for examining the presence of a plurality of analytes, said method comprising the steps of:
    a. providing the Western blotting apparatus of claim 1,
    b. adding reagents into each compartment wherein said reagents specifically bind said analytes at the center portion of said compartment on said analyte support; and
    c. detecting the reagents bound to said analyte support wherein the presence of said detected reagents is indicative of the presence of said analytes.

15. The method of claim 14, wherein said analytes are proteins.

16. The method of claim 14, wherein said analytes in the Western blotting apparatus are separated by gel electrophoresis according to molecular weight.

17. The method of claim 14, wherein said analytes in the Western blotting apparatus are separated by gel electrophoresis according to isoelectric point.

18. The method of claim 14, wherein said reagents are antibodies.

19. The method of claim 14, wherein said compartments in said Western blotting apparatus are arranged in zigzag pattern.

20. The method of claim 14, wherein said compartments in said Western blotting apparatus are arranged in a staggered pattern.

21. The method of claim 19, wherein said zigzag pattern has a zigzag step of 0.1 millimeter to 1 centimeter.

22. The method of claim 19, wherein said zigzag pattern has a zigzag step of one-quart-length to one full-length of a compartment.

23. The method of claim 19, wherein said zigzag pattern has a zigzag step of one-half to a three-quart-length of a compartment.

24. The method of claim 19, wherein said zigzag pattern has a zigzag step of approximately one half the length of a compartment.

25. The method of claim 20, wherein said staggered pattern has a stagger step of 0.1 millimeter to 1 centimeter.

26. The method of claim 20, wherein the total length of the stagger steps between the first and the last compartment ranges from one-quart-length to one full-length of a compartment.

27. The method of claim 20, wherein the total length of the stagger steps between the first and the last compartment ranges form one-half to a three-quart-length of a compartment.

28. The method of claim 20, wherein the total length of the stagger steps between the first and the last compartment is approximately one half the length of a compartment.

29. The method of claim 14, wherein the reagents comprise an array of reagents immobilized on a reagent support.

30. The method of claim 29, further comprising the steps of:
    b(i). placing said reagent support and said analyte support on the same side of the separator in said Western blotting apparatus; and
    b(ii). aligning said reagent support with said analyte support in said Western blotting apparatus to allow contact of said reagent with said analyte at the center portion of said compartment on said analyte support prior to said detecting step.

31. The method of claim 29, further comprising the steps of:

b(i). placing said reagent support and said analyte support on the opposite side of the separator in said Western blotting apparatus; and b(ii). aligning said reagent support with said analyte support in said Western blotting apparatus to allow contact of said reagent with said analyte at the center portion of said compartment on said analyte support prior to said detecting step.

\* \* \* \* \*